Figure 1:
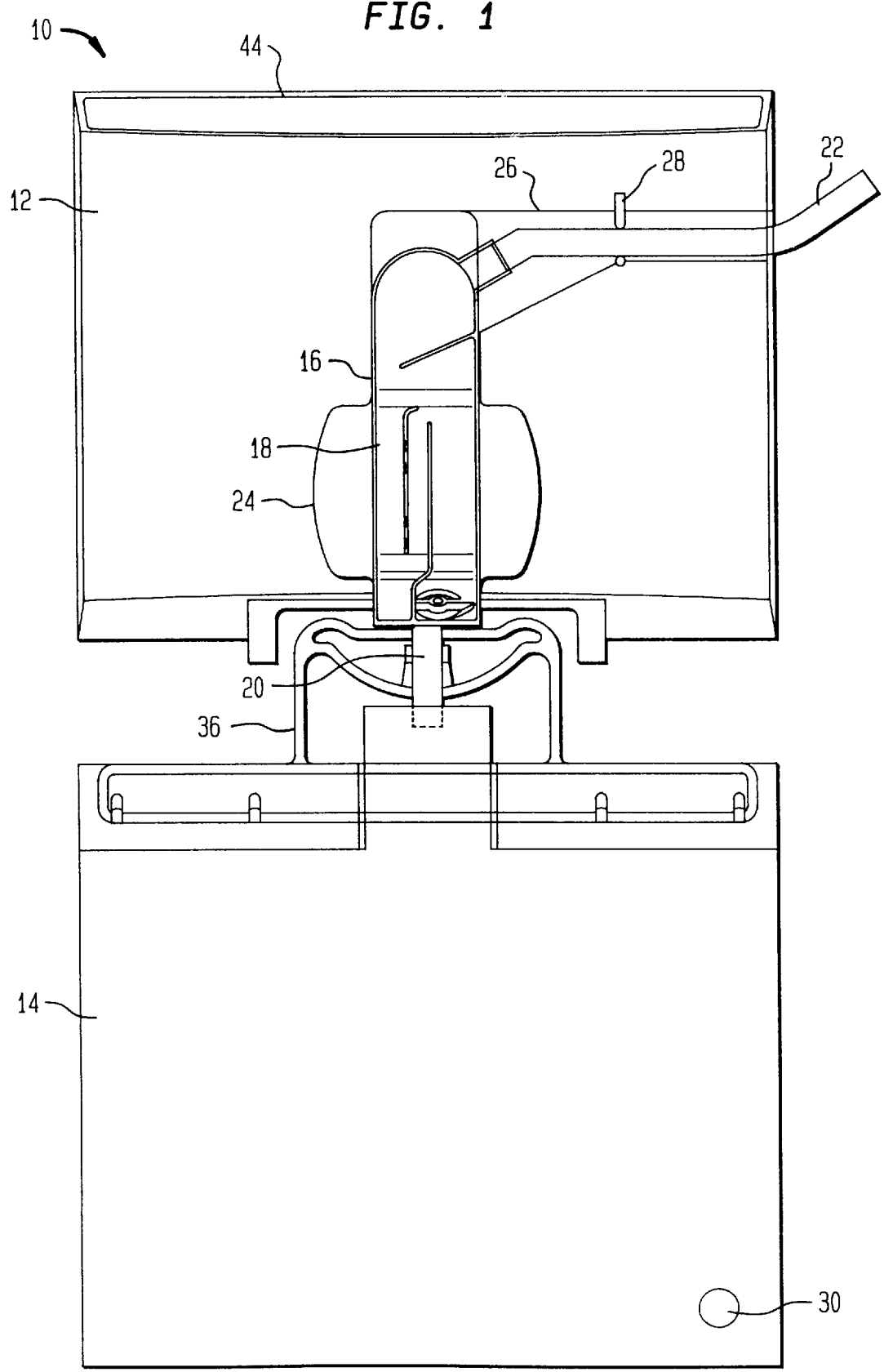

United States Patent [19]

Westphal et al.

[11] Patent Number: 5,769,087

[45] Date of Patent: Jun. 23, 1998

[54] URINE MEASUREMENT APPARATUS AND METHOD FOR THE DETERMINATION OF THE DENSITY OF URINE

[75] Inventors: Detlef Westphal, Oberursel; Klaus Metzner; Günther Grimm, both of Bad Homburg; Uwe Lapp, Hohenahr-Mudersbach; Andreas Wild, Friedberg; Franz-Wilhelm Koerdt, Frankfurt, all of Germany

[73] Assignee: Fresenius AG, Bad Homburg, Germany

[21] Appl. No.: 481,473

[22] PCT Filed: Nov. 8, 1994

[86] PCT No.: PCT/EP94/03671

§ 371 Date: Oct. 19, 1995

§ 102(e) Date: Oct. 19, 1995

[87] PCT Pub. No.: WO95/13524

PCT Pub. Date: May 18, 1995

[30]   Foreign Application Priority Data

Dec. 11, 1993 [DE] Germany ........................... 43 38 687.3

[51] Int. Cl.⁶ ............................................ A61B 5/00
[52] U.S. Cl. ............................................. 128/760; 604/317
[58] Field of Search ................................... 128/771, 760, 128/767, 768; 604/317, 318, 327, 329, 331, 343, 345

[56]   References Cited

U.S. PATENT DOCUMENTS

| | | | |
|---|---|---|---|
| 3,859,854 | 1/1975 | Dye et al. ................................. | 73/215 |
| 4,619,648 | 10/1986 | Rath et al. ............................... | 604/326 |
| 4,712,567 | 12/1987 | Gille et al. ............................... | 128/771 |
| 4,955,879 | 9/1990 | Mervine .................................. | 604/327 |
| 5,211,642 | 5/1993 | Clendenning ............................ | 604/317 |
| 5,380,314 | 1/1995 | Herweck et al. ........................ | 604/317 |

FOREIGN PATENT DOCUMENTS

| | | |
|---|---|---|
| 3240191 A1 | 12/1985 | Germany . |
| 3544031 A1 | 12/1985 | Germany . |
| WO 92 18856 | 10/1992 | WIPO . |

*Primary Examiner*—Max Hindenburg
*Assistant Examiner*—Pamela L. Wingood
*Attorney, Agent, or Firm*—Sterne, Kessler, Goldstein & Fox P.L.L.C.

[57]   ABSTRACT

A body fluid measurement apparatus for continually monitoring the body fluids produced by a catheterized patient is disclosed. The apparatus comprises a discharge hose in fluid communication with the patient, a housing that supports the discharge hose, a dripping chamber for temporarily holding the body fluid while temperature and electrical conductivity measurements are made, a force transducer for producing a signal representing the weight of the body fluid mass collected, a container for collecting the body fluid that is suspended from the force transducer, a storage cell power source, and a computer for processing a signal generated by the force transducer, for generating a timing signal, and for computing the patient's body fluid volume flow in a certain time interval. All computed measurements are sent to a display also located on the apparatus. Additionally, two angle sensors, located in two planes orthogonal to one another, provide a signal to the computer for the compensation of the inclined position of the housing and for the compensation of an erroneous measurement of the weight of the body fluids collected. In addition, a method for the automatic monitoring and recording of the corrected volume flow of body fluids produced by a catheterized patient is also disclosed.

11 Claims, 6 Drawing Sheets

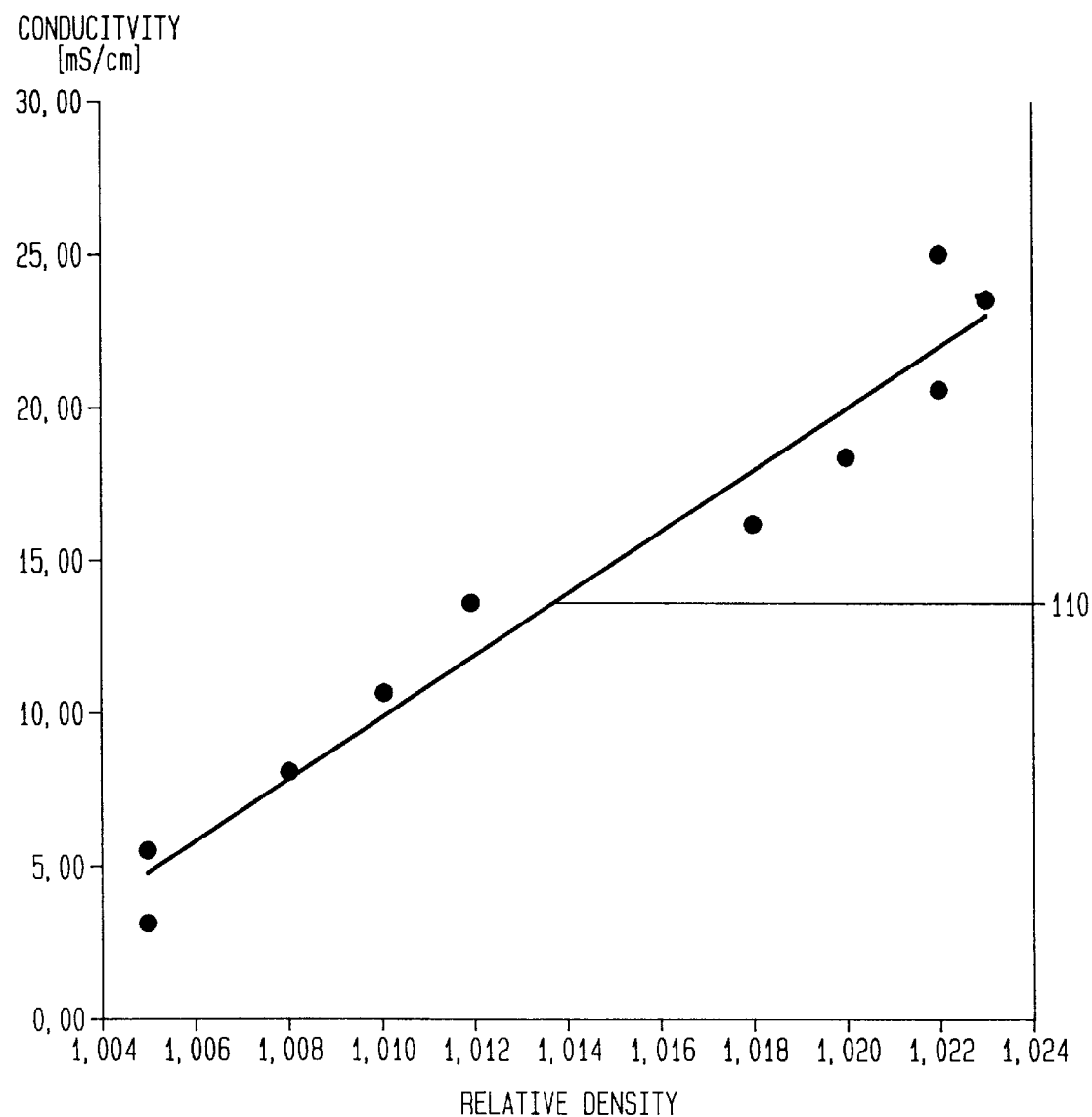

URINE MEASUREMENT APPARATUS AND METHOD FOR THE DETERMINATION OF THE DENSITY OF URINE

DESCRIPTION

The invention concerns a urine measurement apparatus for the automatic monitoring and recording of the urine flow of a catheterized patient in accordance with German Patent No. A-3,544,031.

At intensive care units in hospitals, it is necessary to balance the intake and output of fluids by recording the fluid quantities supplied to the patient, for example, by means of infusions, and comparing with the fluid quantities which leave the body of the patient in a natural manner or via artificial circulations. The most important body fluid which regularly leaves the body of the patient is urine, which is usually voided from the bladder of the patient at intensive care units by inserting a catheter—that is, a tubular delivery element—into the bladder of the patient. A discharge hose is usually connected to the catheter, and the urine flows off through the hose into a collecting container attached to the bed below the patient. In order to prevent a retrograde infection of the hose conduit and thus an infection of the patient, a dripping chamber is arranged within the hose conduit, which interrupts the infection path. Among the most important informative measurement values in which a diagnosing doctor is interested, in connection with urine, is the total volume of the urine excreted within a certain period of time, such as the so-called 24-h urine, the average volume flow of urine within a certain time interval, the specific gravity of the urine, and a visual inspection of the color of the urine.

Among the traditionally used apparatuses are those as are described, for example, in European Patent No. A-0,008,450. The transparent urine collecting bag described there has a scale which helps to determine the collected total volume of the urine. Furthermore, in many hospitals, it is common, as before, that the average urine flow is determined hourly by having a nurse or attendant determine the increase in urine volume every hour and entering it on a chart.

Furthermore, in accordance with the state of the art, the transparent bag permits a visual inspection of the color of the urine, which, however, is complicated by the fact that the collecting bag made completely of transparent material is suspended, in part, below the bed and thus before a background of uniform color, and in addition, hangs so low that the inspecting doctor or attendant has to bend down.

The determination of the density of the urine was carried out frequently in the past by means of test rods, whose end is coated with a substance that corresponds to the electrolyte contained in the urine and brings about a change in a color indicator. Although the density of the urine thus determined is relatively inaccurate, informative clues for the functioning of the kidneys of the patient are produced for the attending doctor. The density can be determined in this way because the density of the urine is influenced primarily by the quantity of the electrolytes contained in the urine due to the heavy Cl ions and less due to the nonelectrolytes, also contained in the urine—including, in particular, urea.

It is obvious that the manual method described above is very expensive and moreover, brings about the disadvantage that a person making observations must inspect the urine collecting bag at certain times. Generally, with the time pressure and lack of personnel always prevailing at intensive care units, there are occasional forgotten measurements, etc., so that the method described is unsatisfactory as a whole.

From European Patent No. A-0,471,413, another example is known for a transparent urine collecting bag, with which only a manual recording of the desired characteristic values is possible.

Therefore, there has been no lack of proposals in the past, in particular, as to how it may be possible to automatically record the total volume of the urine collected and to determine the values for the average volume flow of urine within a certain time interval.

Most solution proposals are based on the idea of recording the urine volume collected in the urine collecting bag by means of a physical auxiliary quantity.

An example of such an apparatus is found in German Patent No. 3,240,191, in which the position of the liquid level in the urine collecting container is to be recorded by means of an ultrasound source. This technique is expensive and susceptible to error, since, on the one hand, a small relative error in the determination of the liquid level brings about a relatively large absolute error in the volume determination, and furthermore, it must be ensured that the liquid level runs perpendicular to a defined axis—that is, it must be ensured that the apparatus does not tip over. It is specifically the latter requirement which frequently cannot be met at intensive care units.

From German Patent No. A-4,023,336, an apparatus is known for monitoring urine, in which the filled volume of the urine collected in a measurement chamber is measured in capacitance, wherein the liquid level of urine influences the capacitance of a measuring capacitor. The disadvantage in this technique is that such a construction is not suitable for a disposable part, since this would be too expensive. When using such a system constantly, it is necessary to clean the measurement chamber and the measuring capacitor frequently, since there may otherwise be a false measurement result because of the deposits being formed. In general, one can see that most proposed systems for monitoring a urine flow are not suitable for the construction of a cheap disposable part, which can be disposed of after use, since the physical principles used presuppose measurement sensors, which come into direct contact with the urine.

From U.S. Pat. No. A-4,343,316 and European Patent No. A-0,109,373, two examples for another measurement principle used in the state of the art are known, in which in the first case, a chamber volume closed off by two solenoid valves is used to measure a certain quantity of urine, and in the second case, a measurement volume of urine between two rolls of a hose pump is measured. The number of chamber volumes measured off is used thereby to determine the total volume of collected urine. The disadvantage with both known apparatuses is that the actuation of the solenoid valves or the operation of the hose pump involves a relatively high expenditure of energy, which must, moreover, be produced continuously. For this reason, it is not possible to construct an automatic urine measurement apparatus, which dispenses with a power supply by means of a power cable, with the last-described principles. It has become evident, however, that the number of cables to a hospital bed of an intensive care unit is already so great with the current state of the art that intensive care unit personnel and doctors prefer an apparatus which works independently—that is, can be operated without a power cable. From the viewpoint of simplifying the operation, it is particularly desirable that an apparatus operated without a power cable have an operating period which corresponds to an average period of treatment of an intensive care unit patient. An operating period for the apparatus of over at least two weeks is desirable, before a storage battery cell, or something similar, must be replaced.

Furthermore, from U.S. Pat. No. A-4,745,929, an apparatus is known, in which the liquid level of a urine column is monitored by means of a number of light barriers, which are arranged alternately one above the other. The disadvantage with this apparatus is similar to that of other apparatuses already described in that valve devices actuated by means of solenoids are needed, which require a high power consumption and accordingly, make the construction of the urine measurement apparatus impossible without a constant-current supply by means of a power cable.

From European Patent No. A-0,073,156, another apparatus to measure urine flow is known, which also monitors the filling of a measurement chamber by means of an optical detector and in which a pump is subsequently turned on. As with other apparatuses already described, the disadvantage here is that the construction expenditure and power consumption is excessively high, so as to construct a measurement apparatus, which takes into account the operating routine of an intensive care unit.

German Patent No. A-3,544,031, which was already mentioned, is regarded as generic. This publication describes an apparatus for the measurement of the weight of the liquid (urine). A computer determines the specific gravity, the temperature, the volume, and the time from the electrically converted signals. It is problematic, however, if the housing or its holder does not hang exactly perpendicular, since, namely, the weight measurement is then fraught with errors.

The goal of the invention therefore is to refine a generic urine measurement apparatus so that an inclined position of its housing or of the holder of the urine measurement apparatus and thus an erroneous measurement of the weight is compensated for.

The goal is attained with a generic urine measurement apparatus, characterized by the fact that two angle sensors arranged in two planes which are perpendicular with respect to one another are provided, and a signal for the inclined position of the holder is generated from them, a correction of the value determined by the force transducer is undertaken for each plane in a computer by means of trigonometric functions, in order to determine the actual weight of the collecting container suspended on the force transducer and the urine collected in it and to generate a signal representing this value, the computer reduces this signal by a stored value for the tare weight (weight of the collecting container) and the value thus obtained is divided by a stored or determined value, which corresponds to the volumetric weight (the specific gravity) of the urine, and indicators to indicate the determined values for total collected urine volume and average urine volume flow in a certain time interval are provided.

Among other things, the invention is based on the knowledge that an electrical force transducer can be operated with very low auxiliary energy, for example, in the form of a strain gauge (DMS).

Furthermore, the invention makes use of the knowledge that the two values which are additionally needed for the determination of the urine volume from the weight of the urine quantity, fluctuate only within such small limits that they can be assumed as constants for this purpose within the framework of accuracy which must be required in a medical routine. The first of these influencing parameters is gravity, which fluctuates slightly as a function of geographic latitude. The second value is density. The density standardized with the density of distilled water fluctuates in human urine between 1.001 to 1.035. This relative error leads to a relative error which is smaller than 2%, or in small quantities (0–100 mL), smaller than 2 mL, in the determination of the urine volume in the manner described. The value thus obtained, therefore, is smaller than the accuracy which can be attained with the traditional scale of urine measurement containers found on the market.

In accordance with the invention, furthermore, it can also be provided that the values for average acceleration due to gravity and average density of human urine, discussed above, are combined to one value—that is, the average volumetric weight.

Furthermore, the invention provides the urine measurement apparatus with a timer, so that the volume increase in the urine collecting bag can be determined after the expiration of certain time intervals. An average volume flow for a certain time interval is determined using the computer to divide the determined volume increase of the urine in the time interval by the length of the time interval. Advantageously, the determined values for total volume and average volume flow in the individual time intervals are indicated in an alphanumeric indicator and filed in appropriate storage sites for later use. It can also be provided that the determined characteristic values be printed via a printer interface and thus that a record be prepared.

Furthermore, it is provided in particular that the aforementioned timing generator be combined with a current economy switch, which switches on the essential current consumers of the urine measurement apparatus only for the pertinent actual measurement at the end of the interval. In this way, the current consumption is further reduced, so that in connection with the sensors already designed to economize in current, such a low current consumption of the total apparatus is attained that a supply of current from the incorporated storage battery cells is made possible. In this way, a power cable can be dispensed with and an autonomously operating apparatus is made possible, which, for example, suspended on the hospital bed, can be transported with the patient, without having to disconnect power cables, or the like.

The design of a urine measurement apparatus in accordance with the invention, however, makes possible not only a current-economizing operation of the urine measurement apparatus and thus a power outlet-independent supply of current, but it also makes construction of the urine collecting container in the form of a plastic bag possible, which is connected, as one piece, with a plastic hose leading to the catheter and can be produced cheaply as a disposable or expendable part. Provision can be made, in particular, to have a dripping chamber in the discharge hose, as it is know, from the state of the art, so as to prevent a retrograde infection of the entire system. This dripping chamber can also be made of plastic and be connected, as one piece, with the two other components—that is, the plastic bag as the urine collecting container and the discharge hose. In this way, a closed system is created, which offers a great degree of security against infection, which can be produced cheaply as a disposable part and which, nevertheless, makes an accurate, automatic recording of the explained characteristic values possible.

In order to determine, in addition to the total urine volume and to the average volume flow in a certain time interval, the density of the urine with an accuracy which corresponds at least to the accuracy of the previously used chemical test rods, it is advantageous to provide that the electrical conductivity of the urine be measured, preferably by means of a four-electrode arrangement, which is, in fact, known, and that the specific gravity of the urine be deduced from the conductivity via a functional connection filed in storage units of the calculating unit. The invention is based here on the surprising knowledge that the specific gravity is influenced almost exclusively by the fraction of electrolytes within the framework of accuracy, as is required in medicine for diagnostic purposes, whereas the nonelectrolytes contained in the urine, such as urea and glucose, influence conductivity and density only to a minor extent. For the determination of the conductivity of the urine, an integratable conductivity measurement apparatus can be used with four electrodes, as is known, for example, from German Patent No. 4,113,033 (Offenlegungsschrift).

Preferably, the measurement arrangement for the conductivity, consisting of four electrodes, is integrated into the dripping chamber. In order to have available a sufficient, electrode-wetting measurement volume of urine for the conductivity measurement, which is constantly replaced, so that, in fact, the new urine which has dripped in the meantime is measured for its conductivity, provision is preferably made, in accordance with the invention, so that the dripping chamber has a U-shaped channel section, whose branch, which is placed vertically, is arranged in the drop fall line of the dripping chamber, and whose other branch leads to an overflow space. Provision is preferably made that the U-shaped channel in the dripping chamber be at least partially limited by intermediate walls, wherein the four electrodes are preferably constructed in the form of lead strips and are bonded into one of these intermediate walls. Preferably, the lead electrodes protrude in the form of elastic tongues over the back wall of the dripping chamber and are used to make contact with corresponding contact points, which are connected with the measurement apparatus.

Preferably, it is also provided that the dripping chamber be made of white plastic and that the front wall of the dripping chamber be made of transparent plastic. In this way, the urine volume in the U-shaped channel can be visually inspected in a simple manner, without the diagnosing doctor having to bend over excessively or being irritated by a background of another color, which can be seen through the urine to be observed.

Furthermore, it can be preferably provided that the dripping chamber be inserted into the measurement apparatus and fixed in it, so that the dripping chamber serves as a strain relief and in this way ensures that no forces which could cause false measurement results of the force transducer are introduced via a connecting hose section placed between the dripping chamber and the urine collecting bag. It is also preferably provided that the urine measurement apparatus has a housing, in which a vertically located affixing shaft is arranged in the form of a channel-like recess, in which the dripping chamber can be locked. In this way, a strain relief is created, on the one hand, and on the other hand, the dripping chamber made of plastic is placed in a snug and closed off manner in the affixing shaft with the surface of the housing, so that, on the one hand, a pleasant appearance is attained, and, on the other hand, the dripping chamber is protected from accidental damage.

It is preferably provided that on the back of the dripping chamber, elastic tongues are constructed, which engage around an affixing projection located in the affixing shaft of the casing. This design offers the advantage that an affixing possibility is created, which can be produced cheaply in large numbers, together with the dripping chamber. Preferably, finger gripplug depressions are provided in the housing of the urine measurement apparatus in addition to the vertical affixing shaft, to the right and left of the inserted dripping chamber; the depressions permit the inserted dripping chamber to be grasped with thumb and index finger and removed from the urine measurement apparatus.

In order to further correct the value for the specific gravity of the urine, determined from the conductivity of the urine in accordance with the invention, provisions can be made for the measurement of the temperature of the urine volume in the dripping chamber. It is preferably provided that at least one of the electric contact points of the affixing base in the affixing shaft of the housing be constructed in such a way that it conducts heat well and is connected with a temperature sensor. This can be, for example, an NTC or PTC resistor. With a good heat-conducting design, the temperature of the electric contact point and thus of the temperature sensor, after a certain time, will correspond to the temperature of the tongue pressing on it in an elastic manner or of the pertinent lead electrode with the urine in the dripping chamber flowing around it.

It should be stressed that even in this measurement value recording, the goal of the invention is taken into account, wherein the component which comes into direct contact with the urine is to be constructed in a manner which is as simple and low-cost as possible. In particular and in accordance with the invention, the number of parts to be constructed is reduced, since one of the four electrodes is, moreover, assigned the task of heat conductor, in addition to electric conduction.

Advantageously, an apparatus for the measurement of body temperature of the catheterized patient can be integrated into the urine measurement apparatus in accordance with the invention by integrating the tip of the catheter, a temperature measurement element—for example, in the form of an NTC or PTC resistor, which is connected via an electric conduit, which can perhaps also be integrated into the discharge hose, with the urine measurement apparatus.

The measurement apparatus described here with the aforementioned features is primarily conceived for the recording of urine characteristic values, but a use for other body fluids is not ruled out.

Figure 2:
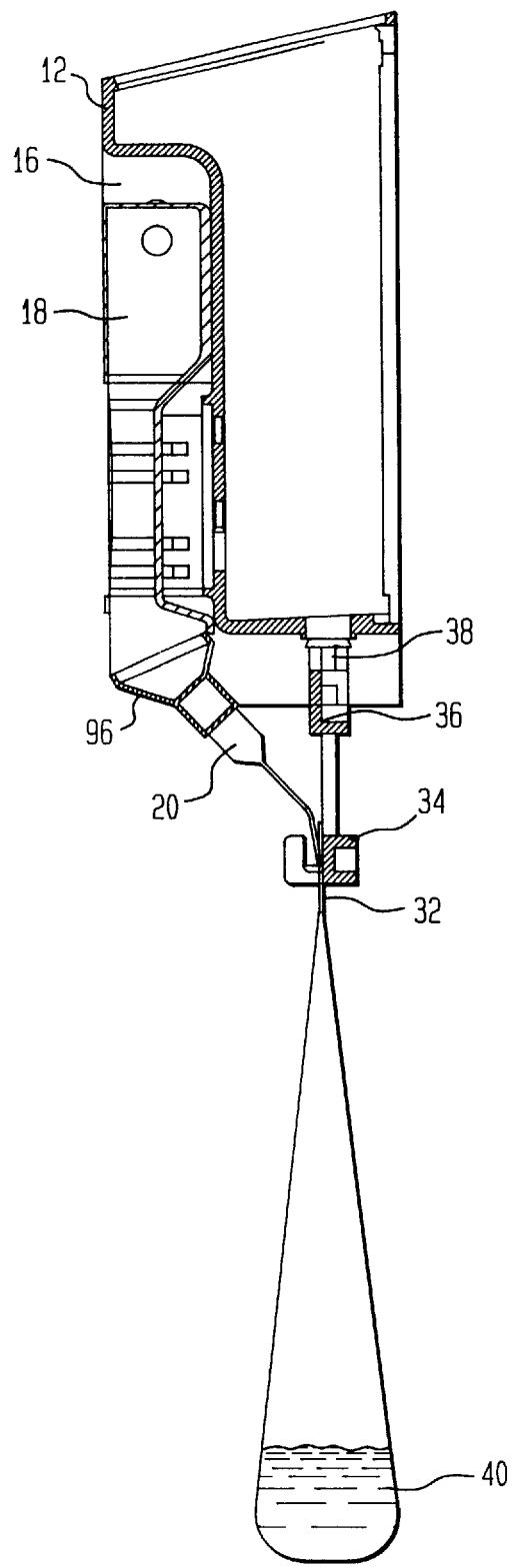
Figure 3:
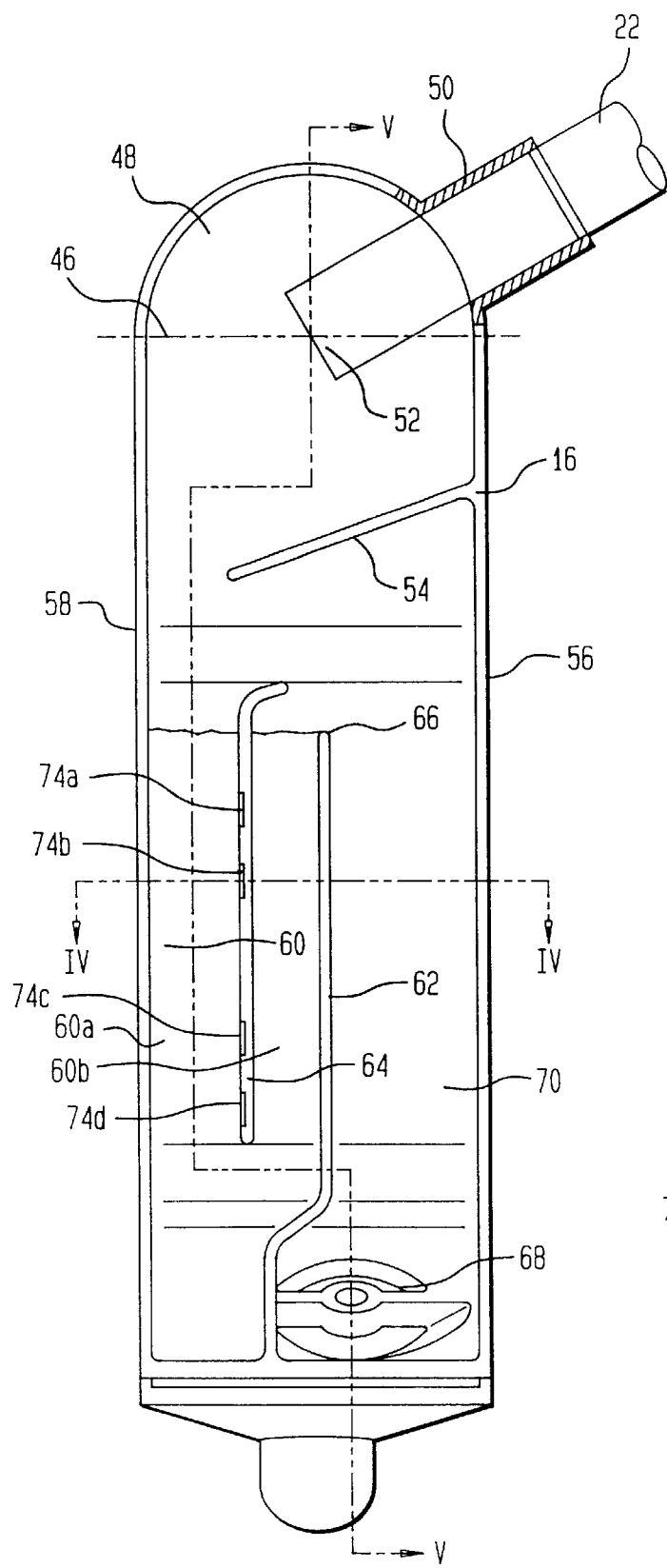
Figure 4:
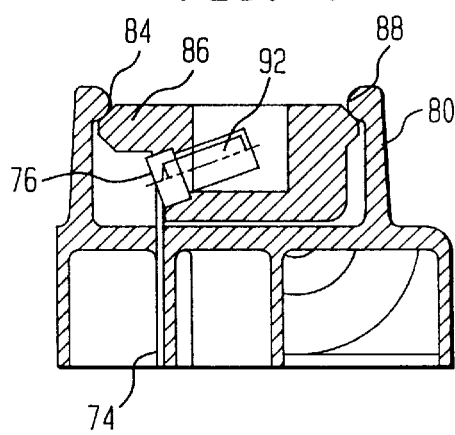
Figure 5:
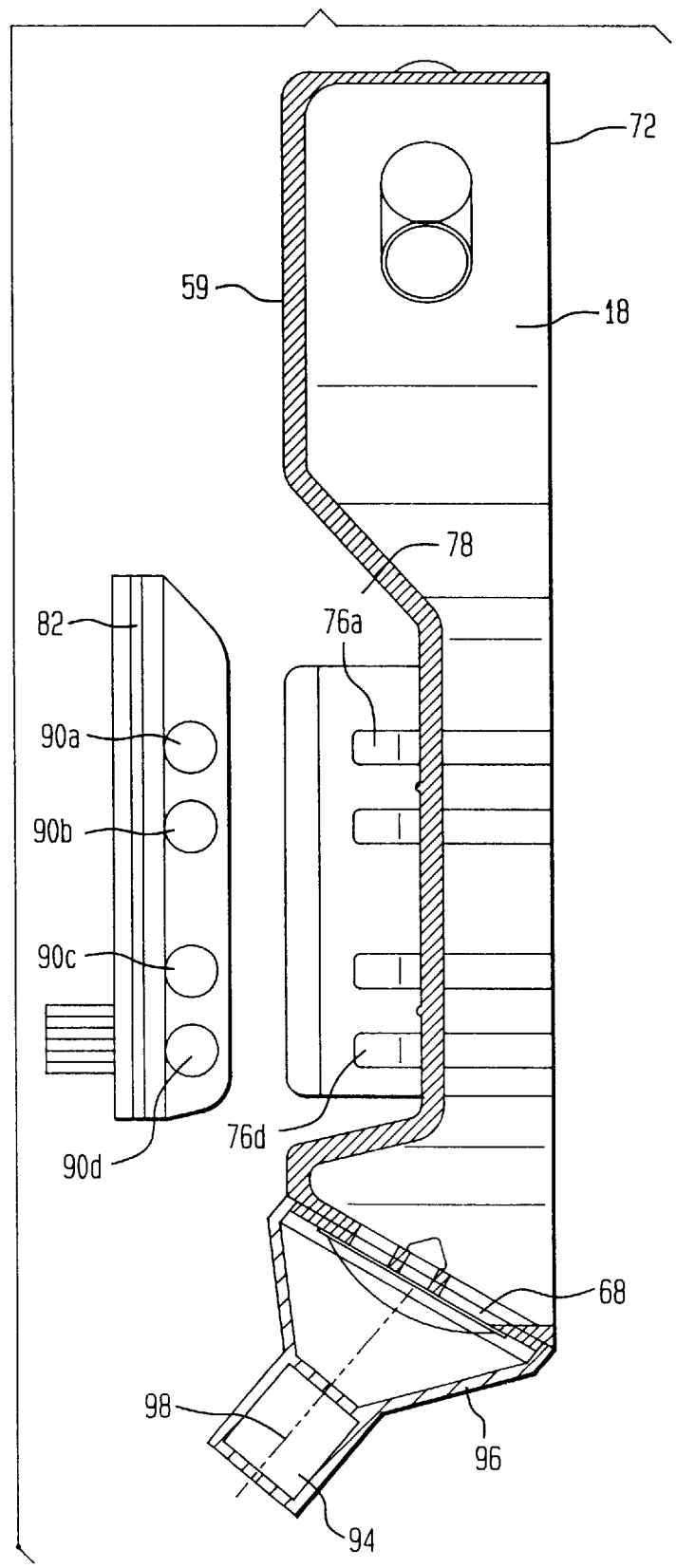
Figure 6:
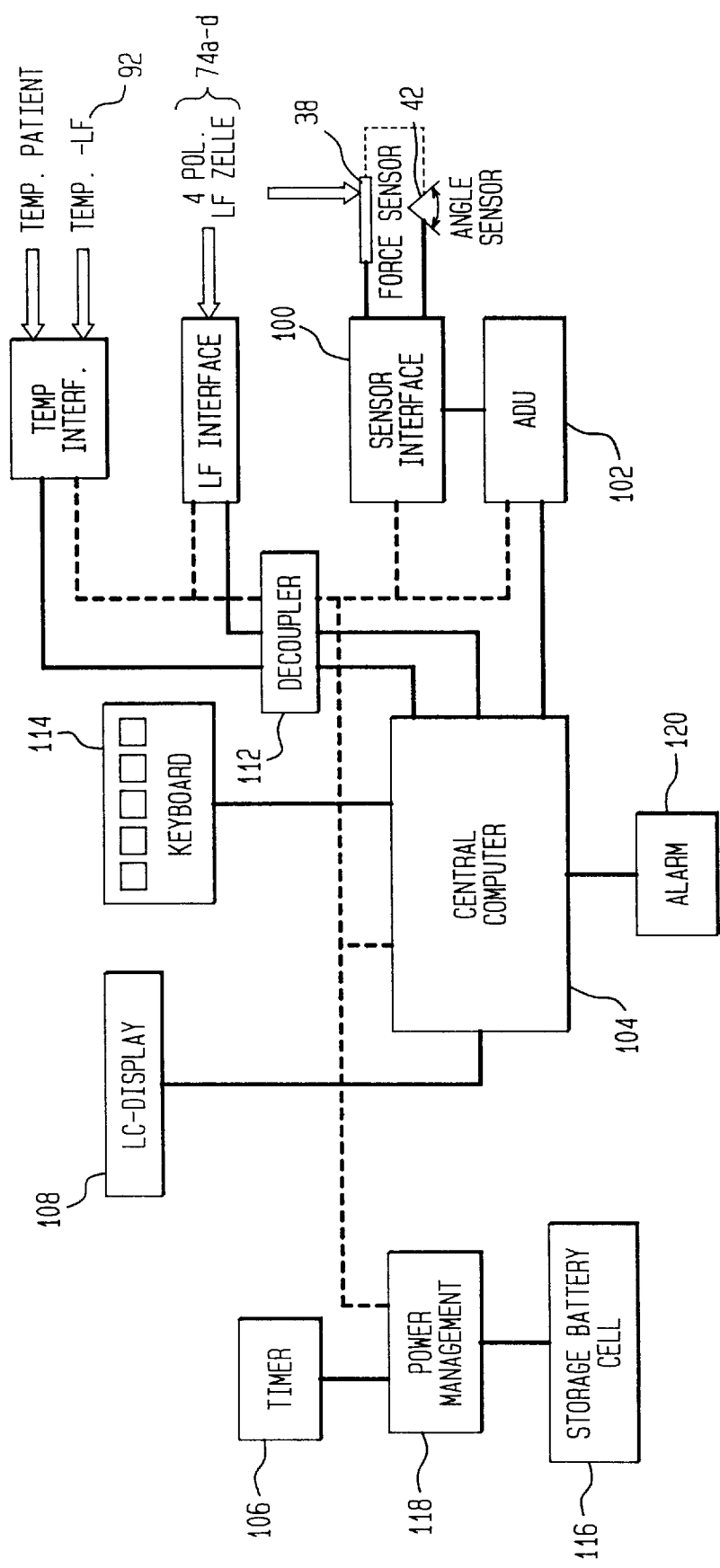

The invention is more closely explained below with the aid of an embodiment shown in the drawing. The drawing shows the following:

FIG. 1, a view of a urine measurement apparatus, in accordance with the invention, with an inserted dripping chamber and suspended urine collecting bag;

FIG. 2, a section through the arrangement shown in FIG. 1;

FIG. 3, a view of the dripping chamber shown in FIG. 1, on an enlarged scale;

FIG. 4, a section along line IV—IV in FIG. 3;

FIG. 5, a section through the dripping chamber along line V—V in FIG. 3;

FIG. 6, a block diagram of the electrical components of the urine measurement apparatus; and FIG. 7, a schematic representation of the connection between relative density and the electrical conductivity of human urine, measured with the accuracy of conventional test rods. The The urine measurement apparatus 10 shown in FIG. 1 has a housing 12, which is affixed to a longitudinal or transverse support of a hospital bed by means of an affixing device, which is not depicted, in such a way that a given distance to the floor remains, which makes it possible to place a urine collecting bag 14, freely suspended below the housing 12, without the bag being on the floor. The housing 12 has an affixing shaft 16, in which a replaceable dripping chamber 18 is affixed. The dripping chamber can be kept in the affixing shaft in various ways—for example, magnetically or by means of a form-locking device, as explained in more detail with the aid of FIGS. 3 to 5.

A hose section 20, which connects the dripping chamber with the urine connecting bag 14, is joined to the lower end of the dripping chamber 18. A discharge hose 22, which leads to the nondepicted catheter placed in the bladder of the patient is joined to the upper end of the dripping chamber 16. The urine conducted away from the bladder of the patient through the catheter flows—since the urine measurement apparatus affixed to the bed frame is lower than the patient—under the influence of gravity through the discharge hose 22 into the dripping chamber 18, from there, through the hose section 20, and is collected in the urine collecting bag 14. Discharge hose 22, dripping chamber 18, connecting hose section 20, and urine collecting bag 14 are made of plastic and bonded to one another. Together, they form one disposable part, which can be thrown away after an operating time of approximately two weeks or one patient change or can be taken to a plastic recycling site.

The affixing shaft 16 of the housing 12 extends to the right and left of the dripping chamber 18 via a certain height of the affixing shaft to finger gripping depressions 24, which make it possible to remove the dripping chamber. A narrower reception channel 26 for the discharge hose 22 is connected to the upper end of the affixing shaft 16 at essentially right angles. Clamping devices 28, with which the discharge hose 22 can be affixed, are placed in the reception channel 26.

The urine collecting bag 14 can have a discharge valve 30, with which an emptying is possible in one of the two lower corner areas. The urine collecting bag preferably has a volume between 2 and 4 L and can thus take up the average 24-h urine of a patient.

At its upper edge 32, the plastic bag 14, which is preferably produced in an extrusion process, is reinforced with a plastic transverse strip 34, which has a U-shaped cross section. The transverse strip 34 is converted, in one piece, into a stirrup-shaped holding device 36, which is connected, in a force-locking manner, with the force transducer 38. In the embodiment under consideration, the stirrup-shaped holder 36 is suspended in a hook connected with the force transducer 38. The force transducer 38 is connected with a holder, which is connected with the bed frame. In the embodiment under consideration, the holder and a housing 12 are constructed in an integral manner. The force transducer 38 can be constructed, for example, in the form of a strain gauge (DMS). The weight introduced into the housing or the holder 12 by the mass of the plastic bag 14, the reinforcement strip 34, the holder 36, and the urine 40 collected in the bag 14 can be measured by the force transducer 38, provided that the action line of the force transducer 38 is directed vertically. In order to compensate for deviations of the action line of the force transducer 38 from the perpendicular, two angle sensors 42 (FIG. 6) placed in two planes which are perpendicular with respect to one another are provided, by means of which an erroneous placing of the entire housing 12 and thus of the force transducer 38 can be compensated for by correcting the signal delivered by the force transducer 38 by multiplying by the cosine of the pertinent erroneous angle.

As can be seen from the view of FIGS. 1 and 2, the dripping chamber 18 locked in the affixing shaft 16 assumes the function of a strain relief. Forces acting on the discharge hose 22—for example, because of a movement of the patient—do not lead to an introduction of force into the connecting hose section 20, so that the weight of the collecting bag 14 can apparently not be reduced. Furthermore, through a corresponding excessive length of the connecting hose section 20, it is ensured that the total weight of the collecting bag 14 is introduced exclusively into the force transducer 38 via the holding device 36, without additional storage forces being produced on the connecting hose section 20, which would cause false results.

The values determined for the total volume 40 of the collected urine, and for calculated, average urine volume flows in individual time intervals, total measurement time, etc., are indicated in an alphanumeric indicator 44. The alphanumeric indicator 44 can consist, among other things, of an LCD dot matrix, in a manner which is in fact known.

FIGS. 3 to 5 show the replaceable dripping chamber 18 of the urine measurement apparatus in an enlarged scale. The dripping chamber 18 combines several functions in itself. First, the free fall stretch of the urine drops will prevent a retrograde infection of the discharge hose 22 and thus an infection of the patient, as is common also in other urine measurement apparatuses, known from the state of the art. The basic geometric shape of the dripping chamber essentially corresponds to that of a parallelopiped, wherein a circular cylinder half 48 is mounted in the area of the imaginary upper base 46. A connecting tube 50, into which the discharge hose 22 has been bonded, joins the circular cylindrical section 48. The discharge hose 22 protrudes, to a certain extent, into the dripping chamber, approximately up to the center line of the essentially parallelopiped dripping chamber. An impact plate 54, placed at an angle to the horizontal and connected on one side with a side wall 56 of the dripping chamber, is located below the opening 52 of the hose 22. The impact plate 54 ends at a certain distance from the opposite side wall 58 of the dripping chamber, so that the urine dripping from the opening 52 of the discharge hose 22 falls onto the impact plate 54 and then flows off because of the inclination of the plate. The urine flows from the impact plate 54 and falls into a U-shaped channel 60, which is limited by the side wall 58 of the dripping chamber and by a first intermediate wall 62. The two branches 60a and 60b of the U-shaped channel are separated from one another by a second intermediate wall 64. The urine dripping from the impact plate 54 gradually fills up the U-shaped channel 60, wherein as a result of the hydrostatic equilibrium, a similar fill level is formed in the two branches, until the urine level reaches the upper rim 66 of the first intermediate wall 62. More urine dripping from the impact plate 54 into the first branch 60a of the U-shaped channel leads, as a result of the hydrostatic equilibrium, to a corresponding volume of urine flowing over the upper rim 66 of the first intermediate wall 62 and reaching the connecting hose 20 via a check valve 68, from where it flows off into the collecting bag 14. The check valve 68 can be springloaded so that it opens only if the urine level in the overflow chamber 70, defined by the first side wall 56 and the first intermediate wall 62, exceeds a certain value. A siphon effect is attained by the arrangement of the U-shaped channel—that is, there is always a certain liquid volume of urine in the dripping chamber, whose material quantity is constantly replaced. The essentially parallelopiped dripping chamber part, consisting of the two side walls 56 and 58, a back wall 59, a first intermediate wall 62, a second intermediate wall 62, and a mounted circular cylinder half 48, is preferably made of white plastic, whereas the front side 72 closing the dripping chamber on the observer side is made of transparent plastic. In this way, the urine volume is always available for inspection to the observing doctor or intensive care unit attendant; its color can be appraised through the transparent front side 72 in front of the white background.

To measure the conductivity of the urine, four electrodes 74a, 74b, 74c, and 74d, in the form of lead strips, are introduced into the intermediate wall 64; their back part extends over the back wall 59 of the dripping chamber and forms elastic contact tongues 76a to 76d. The four electrodes are used for the conductivity measurement of the urine in the U-shaped channel 60 by means of the known four-electrode measurement method. A current of a defined magnitude is applied to the two external electrodes 74a and 74d by means of a constant-current source; the urine flows through on the stretch between the two aforementioned electrodes. The two internal electrodes 74b and 74c form a tapping possibility for a potential difference which is inversely proportional to the conductivity of the urine. By means of the four-electrode arrangement, the influences of transfer resistances between electrodes and urine, on the one hand, and between contact tongues 76a to 76d and the contact points corresponding to them, on the other hand, are eliminated, so that the dripping chamber can be used over its entire service life of approximately two weeks without a subsequent calibration for the conductivity measurement.

As can be seen from FIG. 5, the back wall 59 of the dripping chamber 18 has a recess 78, in which two elastic tongues 80 are located. In the affixing shaft 16 of the measurement apparatus, there is an affixing base 82, which is shaped to be essentially complementary to the recess 78 and which has two rim areas 86 with two rear cuts 84. The elastic tongues 80 are spread out in the affixing shaft 16 by the rims 86 when they are inserted into the dripping chamber 18 and when pressed further into the dripping chamber in the affixing shaft, engage with correspondingly shaped lugs 88 behind the rear cuts 84. At the same time, the four contact tongues 76a to 76d, which are located on the back side of the dripping chamber 18 between the elastic tongues 80, come into elastic contact with correspondingly shaped contact points 90a to 90d and thus create an electrical connection between an electrode 74a to 74d and the electrical part of the urine measurement apparatus.

As FIG. 4 shows, at least one of the contact points.90a to 90d can be constructed in the shape of a hollow-bored screw 92, which is preferably made of a good heat-conducting material. A temperature measurement element, which is not depicted, for example, in the form of a PTC or NTC resistor is cemented in a heat-conducting manner in the borehole. In this way, a means to measure the temperature of the urine in the U-shaped channel 60 is made possible—that is, the temperature is determined at the same place at which the conductivity of the urine is recorded. The measurement signal delivered by the temperature measurement element in the hollow screw 92 and the determined temperature can be used to correct the value determined from the conductivity for the density of the urine in the chamber.

As FIG. 5 shows, a connecting tube 94 for the connecting hose section 20 is provided at the lower end of the dripping chamber; it is connected with the dripping chamber by means of a funnel-shaped, expanded intermediate component 96 in the area of the check valve 68. The connecting cross section between the funnel-shaped component 96 and the actual dripping chamber 18 is at an angle of approximately 30° so that the central axis 98 of the connecting tube 94 is directed backwards with respect to the front side 72 of the dripping chamber 18. In this way, as can be seen from FIG. 2, a compact hose conduit, which essentially follows the external rims of the measurement apparatus 12, is attained and a transition is created to the affixing area of the urine collecting bag 14.

FIG. 6 shows the basic electrical setup of the urine measurement apparatus in accordance with the invention. The signals delivered by the force sensor 38 and the two angle sensors 42 are recorded in a sensor interface 100 and sent to an analog/digital converter 102. The digitally coded signals are conducted further to a central computer 104, which has integrated storage devices, which have not been depicted in detail. In component 104 designated also as the microcontroller—that is, in the computer—the signal delivered by the force sensor is first corrected by means of the signals delivered by the two angle sensors. If the angle deviation is zero, then the pertinent cosine of the erroneous angle is equal to 1—that is, the signal remains unchanged.

The known weight of the urine collecting bag 14—that is, the total tare weight—is first subtracted from the thus determined value for the weight of the total mass suspended on the force sensor over the holding device 36. The thus obtained value represents the weight of the urine 40 collected in the urine collecting bag. The thus obtained value is divided by a stored value for the average acceleration due to gravity. The thus obtained value corresponds to the mass of the collected urine. This value is divided by a value for the density of the urine and thus leads to a total volume of the collected urine 40.

A clock signal generator? 106 measures the time, and the total volume of the collected urine 40 is determined in the previously described manner in certain time intervals, for example, 3 min. The increase in volume within a certain time interval can be determined from the difference between two stored volumes. The quotient from the determined increase in volume and the time interval produces the average urine volume flow for the pertinent time interval. The pertinent values for total volume and average volume flow for a pertinent time interval are filed in a storage unit and can be indicated alphanumerically in an indicator 108.

As described before, the four-electrode arrangement 74a to 74d in the dripping chamber 18 is used to determine the density. The conductivity of the urine is determined in a manner which is, in fact, known. Then, use is made of a tabularly filed function in the microcontroller, which is shown in FIG. 7.

In the form of measurement points, FIG. 7 shows the connection between the conductivity of human urine and its relative specific gravity, as it is determined by test rods, as they have been used up to now in the state of the art. The measurement rods are coated with a substance which responds to the electrolytes present in the urine and bring about a change in a color indicator in a secondary reaction. The connection given by the test rods is approximated by a compensation function 110 and this function is filed in a corresponding storage unit of the microcontroller 104. In this way, it is possible to determine a value for the relative density of the urine and to indicate it in the indicator 108. The value thus determined is available to the doctor for diagnostic purposes. Moreover, it can be used to increase the accuracy of the volume determination of the collected urine by using a correspondingly corrected value instead of an average value for the density.

Furthermore, it is provided that a signal be produced by means of a temperature measurement element integrated into the hollow screw 92; the signal is proportional to the temperature of the urine in the dripping chamber 18. The temperature influence on the density can also be corrected in the microcontroller by a corresponding correction function in this way.

Furthermore, it is additionally provided that a temperature-sensitive measurement sensor be attached to the catheter, which delivers a signal that is also conducted to the microcontroller via an interface. The signal produced by the temperature measurement element located on the catheter tip is converted into a temperature with a corresponding function and is also available to the monitoring personnel in an indicator 108. This additional function makes a continuous monitoring of the body temperature of the patient possible, without additional apparatus being needed. Furthermore, provisions can be made so that the body temperature of the patient is also documented at certain time intervals determined by the clock signal generator 106 and the measurement values filed in a corresponding storage unit of the microcontroller 104 are documented.

The sensors coming into direct contact with the patient, such as the temperature sensor located on the tip of the catheter or the sensors coming into indirect contact with the patient via a possible conduit within a urine column, such as the four poles of the conductivity meter 74a to 74d, are decoupled from the patient by an electrical decoupling 112 for safety reasons.

The apparatus also has a keyboard 114, with which, for example, a new reference point for the following increase in weight can be set after the emptying of the urine collecting bag 14 through the emptying valve 30. This function is particularly useful if—as described—the bag is emptied daily, for example, but is reused continuously, since the tare weight—that is, the total weight suspended on the force sensor, which is not attributable to the actual collected urine, is slightly greater than the weight of the urine collecting bag 14, the transverse strip 32, and the holding device 36, since the urine collecting bag 14 is not completely emptied during the emptying, but rather urine residues remain, which should not be recorded again during a subsequent measurement cycle.

The electric circuit of the measurement apparatus in accordance with the invention also has a storage battery cell 116, which is used for providing current to the entire apparatus. In order to lower current consumption, a current-economizing circuit 118 is provided, which is controlled by the clock signal generator 106. An operation of the entire apparatus is made possible by the combination of the clock signal generator 106 and the current-economizing circuit 118, in which measurements are undertaken merely at the interval limits of a time interval, so that the current consumption is reduced as a whole to the extent that the use of a storage battery cell as a current source is made possible. In this way, it is possible to dispense with a power cable, which represents a hazard, particularly in intensive care units and when transferring the patient to another bed.

Finally, the circuit according to FIG. 6 has an alarm 120, which is controlled by the microcontroller 104, if the determined values—for example, for urine volume, urine volume flow, body temperature of the patient, or something similar—lie outside certain limit values. The alarm 120 can, for example, release an acoustic signal or an optical signal.

Not depicted in FIG. 6 is an interface to a printer or the like, with which a record of the recorded measurement values can be printed out. Although the urine measurement apparatus, in accordance with the invention, was invented for the automatic monitoring and recording of the urine flow of a catheterized patient, the use of the apparatus for the automatic monitoring and recording of the volume flow of other body fluids is also conceivable.

We claim:

1. A body fluid measurement apparatus for monitoring body fluids produced by a catheterized patient, comprising:
   a housing mountable to a hospital bed;
   a discharge hose connected to said housing and connectable to a catheterized patient disposed on the hospital bed for receiving body fluids produced by the patient;
   a force transducer coupled to said housing;
   a container suspended from said housing and coupled to said force transducer, said container being in fluid communication with said discharge hose;
   at least two angle sensors coupled to said housing and oriented in orthogonal planes to each other to provide a correction signal indicating an inclined position of said housing;
   a storage battery cell, coupled to said housing, providing a current supply; and
   a computer coupled to said force transducer and to said angle sensors to collect and process signals from said angle sensors and from said force transducer, to determine values for total collected patient body fluid volume and average body fluid volume flow in a predetermined time interval, and to generate signals corresponding to said values.

2. The fluid measurement apparatus of claim 1, wherein said computer further comprises:
   a processing unit for continually determining a volume of collected body fluid produced by the patient;
   a timer for providing a timing signal to said processing unit, for determining an average volume flow of the patient's body fluid over a time interval and for determining an increase in body fluid volume;
   a storage unit for storing a value for the average density of body fluid produced by the patient and a value of said average body fluid flow over said time interval; and
   display means, coupled to said housing, and in electronic communication with said computer, for displaying the patient's average body fluid flow values over said time intervals.

3. The fluid measurement apparatus of claim 2, further comprising:
   a power supply for said computer; and
   a switch, coupled to said power supply and to said computer for switching on said power supply after receiving a signal from said clock signal generator after the expiration of said time interval, and for switching off said power supply after said body fluid measurements are performed for said time interval.

4. The fluid measurement apparatus of claim 1, wherein said container further comprises:
   a stirrup-shaped holding device connectable to said container and coupled to said force transducer in a form-locking manner; and
   means for bonding said container to said discharge hose to form a removable and disposable part.

5. The fluid measurement apparatus of claim 1, further comprising:
   a dripping chamber, coupled to said housing and in fluid communication between said discharge hose and said container;
   a shaft connectable to and located within said housing, said shaft having extensions forming a plurality of finger gripping depressions extending around to the right and left of said dripping chamber for removing said dripping chamber;

a means of locking said dripping chamber to said shaft;

a channel joined to said shaft, for guiding said discharge hose from said dripping chamber to the patient, wherein a portion of said discharge hose is in fluid communication between said dripping chamber and said container, and is constructed long enough to form a force-free hose loop; and means for bonding said discharge hose, said dripping chamber, and said container into one piece to form a removable and disposable part.

6. The fluid measurement apparatus of claim 5, wherein said dripping chamber further comprises:

a front wall made of transparent plastic for viewing purposes;

a U-shaped channel with internal front, back, and side walls comprising a branch located in the body fluid drop fall line of said dripping chamber, and another branch leading to an overflow chamber being in fluid communication with said discharge hose and said container; and a check valve, connectable to said dripping chamber and spring-loaded to open only when the fluid level in said overflow chamber exceeds a predetermined value.

7. The fluid measurement apparatus of claim 6, further comprising:

a base with rim areas, located in said shaft; and a plurality of elastic tongues constructed on a back wall of said dripping chamber and engaging said rim areas of said base.

8. The fluid measurement apparatus of claim 7, wherein said dripping chamber further comprises:

a plurality of lead electrodes mountable to at least one side wall of said U-shaped channel extending through said back wall of said dripping chamber, to form elastic contact tongues;

a plurality of contact points corresponding to the number of said electrodes inside said dripping chamber, attachable to said shaft of said housing; and a temperature sensor for sensing temperatures of said body fluid and for providing a temperature signal to said processing unit to generate a corrected value for said density of body fluid produced by the patient.

9. The fluid measurement apparatus of claim 2, further comprising:

a temperature measurement element, coupled to the patient's catheter and to said discharge hose; and means for electrically coupling said temperature measurement element to said computer for providing a temperature reading to be displayed by said display means.

10. A method, for the automatic monitoring and recording of the volume flow of body fluids produced by a catheterized patient, which are captured in a collecting container that is suspended on a holder from a fluid measurement apparatus, comprising the steps of:

determining a weight of the body fluids collected in the container;

determining a correction factor based on signals generated from two angle sensors coupled to the fluid measurement apparatus, oriented orthogonal to each other, that determine a value for an inclined position of the holder;

determining a corrected value of said weight of the body fluids produced by the patient; and determining a value for volume flow of the body fluids by
    subtracting off a stored tare value of the container from said corrected actual weight to produce a value for weight of body fluid collected, and
    dividing said value for weight of body fluid collected by a stored value for the specific gravity of the body fluid, producing a value for the total collected body fluid volume.

11. The method of claim 10, further comprising the step of:

determining a value for density of body fluids through an empirically derived relationship based on a value for measured electrical conductivity of the body fluids produced by the patient.

* * * * *